US007047067B2

(12) United States Patent
Gray et al.

(10) Patent No.: US 7,047,067 B2
(45) Date of Patent: May 16, 2006

(54) APPARATUS, METHODS, AND COMPUTER PROGRAM PRODUCTS FOR EVALUATING A RISK OF CARDIAC ARRHYTHMIAS FROM RESTITUTION PROPERTIES

(75) Inventors: Richard A. Gray, Vestavia Hills, AL (US); Xiaozhong Chen, Birmingham, AL (US); Isabelle Banville, Alabaster, AL (US)

(73) Assignee: UAB Research Foundation, Birmingham, AL (US)

( * ) Notice: Subject to any disclaimer, the term of this patent is extended or adjusted under 35 U.S.C. 154(b) by 595 days.

(21) Appl. No.: 10/160,319

(22) Filed: May 31, 2002

(65) Prior Publication Data

US 2004/0015088 A1   Jan. 22, 2004

(51) Int. Cl.
*A61B 5/452*   (2006.01)
(52) U.S. Cl. ...................................... 600/516; 600/515
(58) Field of Classification Search ................ 600/509, 600/515, 516, 518, 519, 521; 607/9, 4, 14, 607/25
See application file for complete search history.

(56) References Cited

U.S. PATENT DOCUMENTS 5,437,285 A * 8/1995 Verrier et al. ................ 600/515
5,555,889 A * 9/1996 Karagueuzian et al. ..... 600/518
6,370,431 B1 * 4/2002 Stoop et al. .................. 607/14

OTHER PUBLICATIONS

Weiss et al., "Chaos and the Transition to Ventricular Fibrillation, A New Approach to Antiarrhythmic Drug Evaluation," Circulation (1999) 99:2819-2826.
Riccio et al., "Electrical Restitution and Spatiotemporal Organization During Ventricular Fibrillation," Circulation Research (1999) 84:955-963.
Garfinkel et al., "Preventing ventricular fibrillation by flattening cardiac restitution," PNAS (2000) 97 (11):6061-6066.
Millar et al., "Correlation between refractory periods and activation-recovery intervals from electrograms: effects of rate and adrenergic interventions," Circulation (1985) 6:1372-1379.

* cited by examiner

*Primary Examiner*—Kennedy Schaetzle
(74) *Attorney, Agent, or Firm*—Myers Bigel Sibley & Sajovec

(57) ABSTRACT

Methods, systems, and computer program products can be provided for evaluating a risk of the occurrence of cardiac arrhythmias in a heart. The system can include at least one sensing electrode and a controller. The sensing electrode can be configured to sense electrical signals from a heart over a range of heart rates. The controller can be configured to determine values of a at least one restitution property of the heart from the sensed electrical signals and to evaluate the risk of the occurrence of cardiac arrhythmias from the determine values of the at least one restitution property.

30 Claims, 6 Drawing Sheets

APPARATUS, METHODS, AND COMPUTER PROGRAM PRODUCTS FOR EVALUATING A RISK OF CARDIAC ARRHYTHMIAS FROM RESTITUTION PROPERTIES

FIELD OF THE INVENTION

The present invention is related to evaluating a risk of cardiac arrhythmias.

BACKGROUND OF THE INVENTION

Despite advances in antiarrhythmic therapies, cardiac arrhythmias remain a major health problem, causing about 300,000 sudden cardiac deaths annually in the United States (Weiss J N et al., Circulation (1999) 99:2819–2826). Cardiac arrhythmias can occur when the electrical waves which stimulate the heart meander erratically through the heart muscle, creating disordered and ineffective contraction. The primary focus of literature and research has been on detecting when cardiac arrhythmias occur and reducing the occurrence of arrhythmias with medical therapies or lifestyle changes. Medical therapies include drugs which can reduce the occurrence of arrhythmias and implantable devices which can detect the onset of arrhythmias and apply electrical pulses to the heart to stop arrhythmias. However, oftentimes medical therapies are not employed until an individual first suffers and survives a sufficiently serious arrhythmia which signals the need for medical therapy. Consequently, there is a need for techniques and apparatus which can identify individuals at risk for developing cardiac arrhythmias prior to the onset of serious arrhythmia.

SUMMARY OF THE INVENTION

The present invention provides methods, systems, and computer program products for evaluating a risk of the occurrence of cardiac arrhythmias in a heart. In some embodiments of the present invention the methods can include detecting electrical activity from the heart over a range of heart rates (i.e. restitution properties). Values of at least one restitution property of a heart are determined from the detected electrical activity over the range of heart rates. The risk of occurrence of cardiac arrhythmias is evaluated from the determined values of the at least one restitution property.

In further embodiments of the invention, the method can include determining a rate of change of QT time interval values as a function of TQ time interval values. A QT time interval value and a TQ time interval value at which the rate of change is greater than one are identified. An increased risk of the occurrence of cardiac arrhythmias is identified when at least one of the identified QT value and the TQ time value is within a range for which the heart can operate during normal life activities.

According to still other embodiments of the invention, the method can include determining a rate of change of action potential duration values as a function of diastolic interval values. An action potential duration value and a diastolic interval value at which the rate of change of the action potential duration values as a function of diastolic interval values is greater than one are identified. An increased risk of the occurrence of cardiac arrhythmias is identified when at least one of the identified action potential duration value and the diastolic interval value is within a range for which the heart can operate during normal life activities.

According to other embodiments, an increased risk of the occurrence of cardiac arrhythmias is identified when, in response to an abrupt change in the heart rate, the rate of change of the restitution properties is greater than a threshold value.

Other embodiments include a system for evaluating a risk of the occurrence of cardiac arrhythmias in a heart. The system can include at least one sensing electrode and a controller. The at least one sensing electrode can be configured to sense electrical signals from a heart over a range of heart rates. The controller can be configured to determine values of at least one restitution property of the heart, from the sensed electrical signals, over the range of heart rates and to evaluate from the determined restitution property values the risk of the occurrence of cardiac arrhythmias.

According to further embodiments, the controller is configured to identify a restitution property at which the rate of change of a range of restitution properties is greater than a threshold value and to generate a signal which is indicative of an increased risk of the occurrence of cardiac arrhythmias when the identified restitution property is within a range for which the heart can operate during normal life activities.

According to other embodiments, the controller is configured to generate a signal indicative of an increased risk of the occurrence of cardiac arrhythmias when a rate of change of a range of restitution properties, in response to an abrupt change in the heart rate, is greater than a threshold value.

According to still other embodiments, a computer program product may be provided for evaluating a risk of the occurrence of cardiac arrhythmias in a heart. The computer program product can include a computer readable storage medium having computer readable code. The computer code can include program code for receiving electrical signals from a heart over a range of heart rates. Program code can be included for determining values of at least one restitution property of the heart from the electrical activity of the heart over a range of heart rates. Program code can also be included for evaluating, from the determined values of the at least one restitution property, the risk of the occurrence of cardiac arrhythmias.

The foregoing and other objects and aspects of the present invention are explained in detail in the specification set forth below.

DETAILED DESCRIPTION

The present invention will now be described more fully with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

According to some embodiments of the present invention, apparatus, methods, and computer program products are provided for predicting cardiac arrhythmias from the rate dependence of cardiac restitution properties. Restitution properties can include parameters for describing the adaptation of a heart to different heart rates, such as action potential duration, diastolic interval, QT time interval, TQ time interval, and T wave duration all of which are discussed below. It will be understood that operations depicted in the figures, and combinations thereof, may be implemented using one or more electronic circuits, such as circuits included in a electrocardiogram (ECG) instrument, implantable device such as a cardiac pacemaker, or other electronic components for sensing or providing cardiac electric fields. It will also be understood that the invention is applicable to humans and animals. It will also be appreciated that, in general, operations depicted in the figures, and combinations thereof, may be implemented in one or more electronic circuits, such as in one or more discrete electronic components, one or more integrated circuits (ICs) and/or one or more application specific integrated circuits (ASICs) and/or application specific circuit modules, as well as by computer program instructions which may be executed by a computer or other data processing apparatus, such as a microprocessor or digital signal processor (DSP).

The computer program instructions may also be embodied in the form of a computer program product in a computer-readable storage medium, i.e., as computer-readable program code embodied in the medium for use by or in connection with an instruction execution system. The computer-readable storage medium may include, but is not limited to, electronic, magnetic, optical or other storage media, such as a magnetic or optical disk or an integrated circuit memory device. Accordingly, FIGS. 1–9 provide support for the development of electronic circuits and other apparatus that perform the specified operations, acts for performing the specified operations, and computer program products configured to perform the specified operations.

Figure 1:
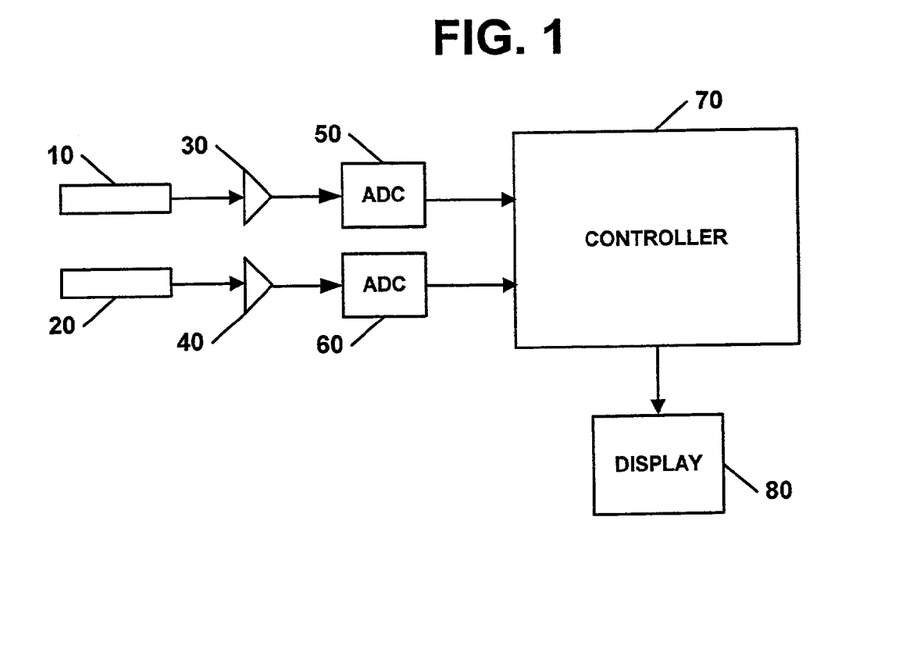
FIG. 1 is a block diagram of a system for predicting the risk of occurrence of cardiac arrhythmias according to some embodiments of the present invention.

FIG. 1 shows a block diagram of a system for evaluating the risk of occurrence of cardiac arrhythmias according to some embodiments of the present invention. The system may include pairs of sensing electrodes 10 and 20, amplifiers 30 and 40, analog-to-digital converters 50 and 60, a controller 70, and a display 80. Although two electrodes are shown for illustration purposes, the invention is applicable to any number of electrodes and any manner of sensing electric signals of a heart. The electrodes can be connected via a catheter to muscle tissue of a patient's heart to detect electrical signals caused by the depolarization and repolarization of the heart. In other embodiments, the electrodes 10 and 20 can sense the heart's electrical signals from the surface of the patient's body, in a non-invasive manner, such as can be done with a conventional electrocardiogram (ECG) device. The electrical signals can be also be detected with conventional unipolar, bipolar, or combinations of electrodes having different frequency sensing bandwidths or multi-pole electrodes.

Electrical signals sensed by the electrodes 10 and 20 are amplified by respective amplifiers 30 and 40 and converted to digital signals by respective analog-to-digital converters 50 and 60. The digital signals are provided to the controller 70 which performs operations to evaluate the risk of occurrence of cardiac arrhythmias. The risk of occurrence of cardiac arrhythmias can be displayed on the display 80.

Figure 2:
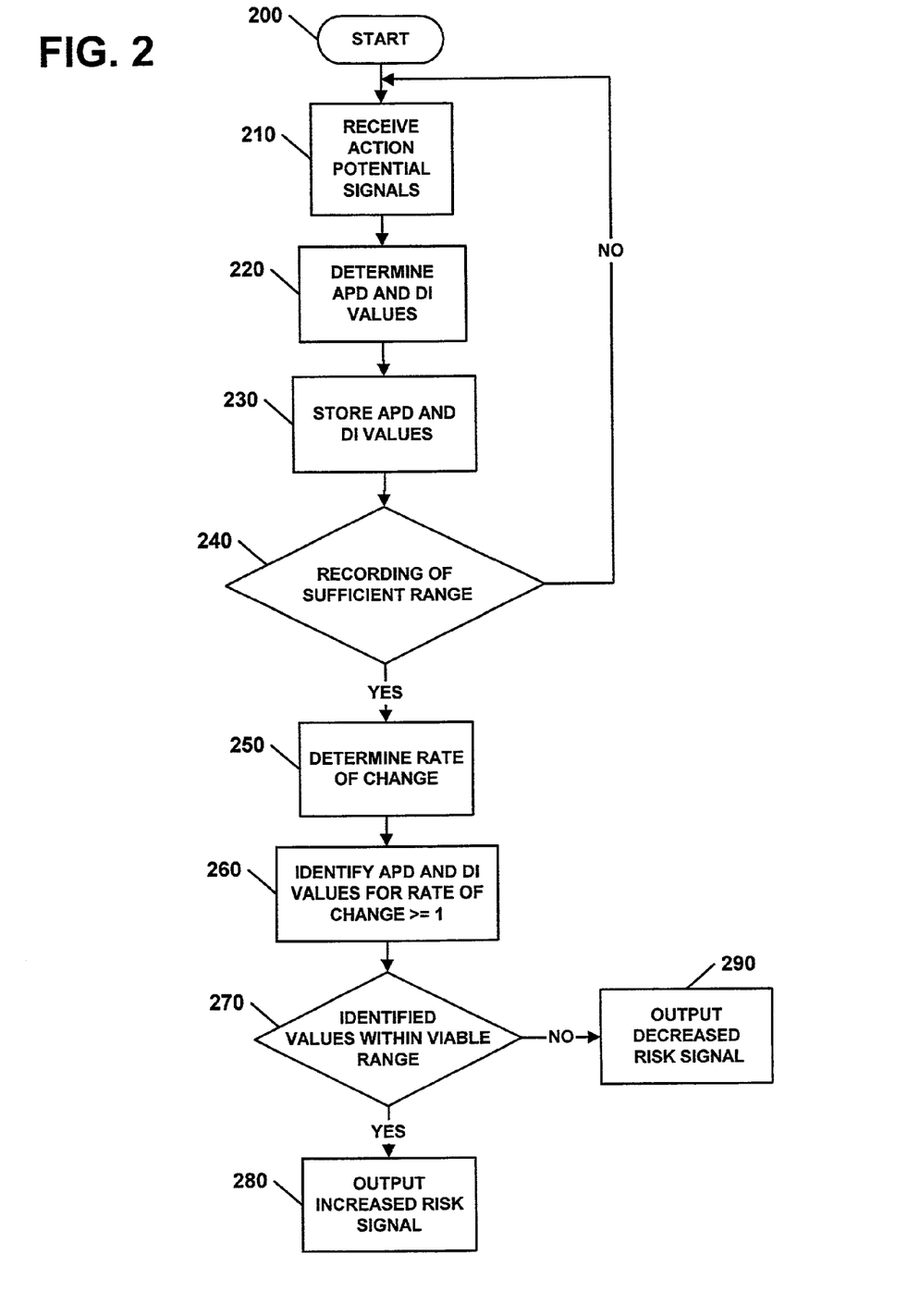
FIG. 2 is a flow chart showing operations for predicting the risk of occurrence of cardiac arrhythmias according to some embodiments of the present invention.
Figure 3:
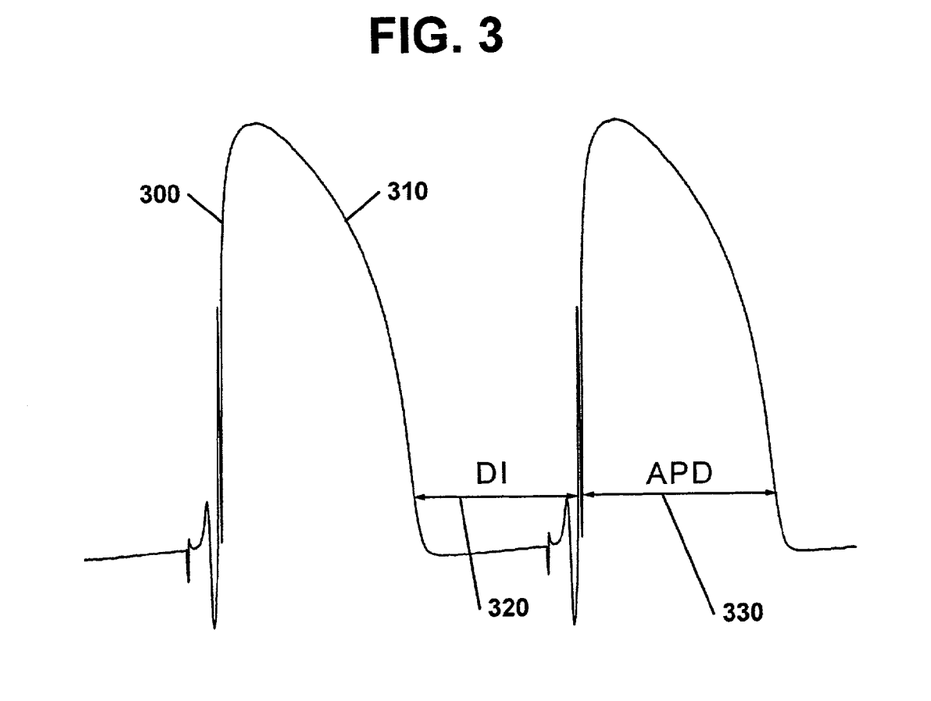
FIG. 3 is a graph showing monophasic action potential signals from a heart.

According to some embodiments of the present invention, the operations for evaluating the risk of cardiac arrhythmias can include those shown in FIG. 2 beginning at Block 200. At Block 210 electrical signals are received which can be indicative of the action potential of the heart, such as the sampled monophasic action potential signals illustrated by the graph in FIG. 3. The increasing signal waveform at 300 is associated with depolarization of the heart muscle proximate to a sensing electrode and the decreasing waveform at 310 is associated with repolarization of the heart muscle. At Block 220 the diastolic interval (DI) between repolarization and the next depolorization, shown as 320, and the action potential duration (APD) between depolarization and the next repolarization, shown as 330, are determined and then stored at Block 230. Depolarization and repolarization times may also be determined from extra-cellular recordings. Storing may occur only transitionally or more permanently such as in a volatile or non-volatile memory or storage device.

While recordings are being made, the heart is operated or paced over a range of different heart rates. The range of heart rates may vary from a low rate, such as when the patient is at rest, to a much higher rate, such as when the patient is engaged in high physical exertion. Additionally, the range of heart rates may extend from near a minimum rate during normal life activities to near a maximum rate during normal life activities. The heart can operate over a range of rates by having the patient follow a varying exercise exertion profile or by direct electrical stimulation of the heart, such as with signals from a pacemaker. Alternatively, the heart can be chemically induced to pace over a range. Recordings may be taken, for example, after a desired time interval since the last recording or upon the heart settling into a steady state at a desired heart rate.

At Block 240 a decision is made to continue or terminate recordings. The basis for the decision can include completion of a suitable recording over a desired range of heart rates, a desired range of sensed action potentials, completion of a time interval of interest, or an indication from an operator or clinician to terminate the recordings.

Figure 4:
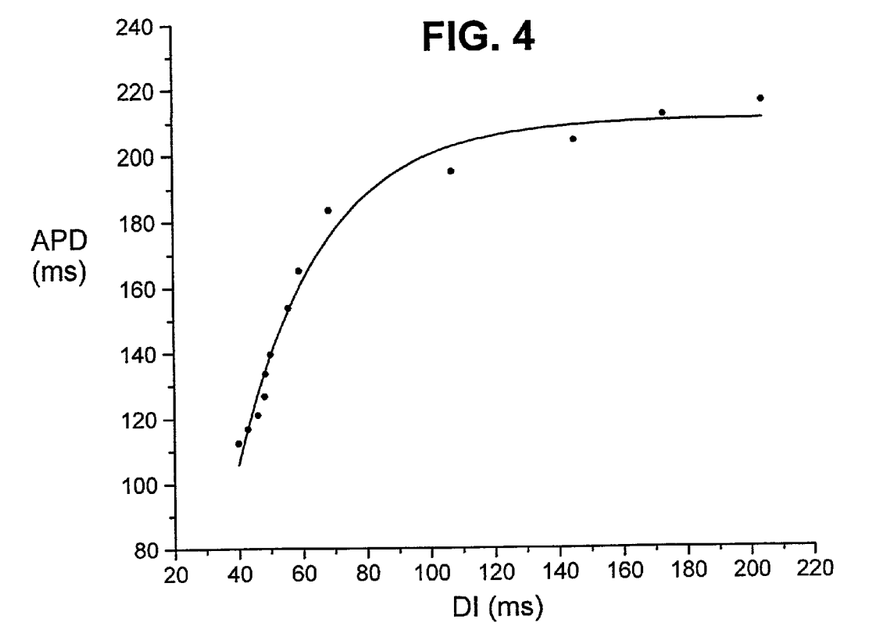
FIG. 4 is a graph showing the relationship of action potential duration to diastolic interval from experimental data.

FIG. 4 shows a graph of an example relationship of action potential duration to diastolic interval from experimental data taken from the right ventricle of a rabbit heart. The heart rate of the rabbit was paced by direct electrical stimulation over cycle lengths from 154 to 420 milliseconds. The individually sampled action potential duration (APD) data points and corresponding diastolic interval (DI) data points along with a curve conventionally fitted through the data points are shown in FIG. 4.

At Block 250 of FIG. 2, the rate of change of the APD values as a function of the DI values is determined. The rate of change can be determined directly from the sampled APD values and DI values by dividing the numerical change in APD values by the change in the corresponding DI values at one or more points. The rate of change can also be determined from the slope of a curve which is conventionally fitted through the APD and DI values, such as illustrated in FIG. 4. The rate of change of APD relative to DI can also be determined from values obtained by interpolation within the range of sampled values or by extrapolation outside of the range of sampled values.

At Block 260 the APD and DI values at which the rate of change is one and/or becomes greater than one are identified (hereafter "threshold APD and DI values"). It has been found that when the rate of change of APD as a function of DI becomes greater than one, that cardiac arrhythmias, such as ventricular fibrillation, can occur and be sustained in the heart.

At Block 270 the threshold APD and DI values are compared to a range of heart rates over which the heart may operate during normal life activities (a viable range). When the threshold APD and DI values occur within an expected viable range of the heart then the patient is evaluated to have an increased risk for the occurrence of cardiac arrhythmias and, at Block 280, a signal indicating the increased or high risk of cardiac arrhythmias (i.e. an increased risk over the occurrence of arrhythmias expected for a patient's age, gender, and physical attributes) is output to the display 80 (FIG. 1). In contrast, when the threshold APD and DI values occur outside an expected viable range of the heart or when threshold APD and DI values are not obtained during a patient's evaluation (i.e., the rate of change remains less than one over the heart rates of interest) then a signal indicating a decreased or low risk of cardiac arrhythmias (i.e., a lower risk than the occurrence of arrhythmias expected for a patient's age, gender, and physical attributes) is output, at Block 290, to the display 80. Alternatively, or additionally, the output indication of the increased or decreased risk may be provided to an electronic or paper patient report.

For example, in FIG. 4, the rate of change of the restitution properties (shown as APD) becomes greater than one at a DI of about 78 milliseconds. The DI of 78 milliseconds corresponds to a long pacing cycle length (about 250 milliseconds) which is within a range of cycle lengths which the heart can be expected to experience under the rabbit's own naturally occurring stimulation of the heart (i.e., a viable operational range). Consequently, the heart used in the experiment can be expected to have an increased risk of the occurrence of cardiac arrhythmias.

According to other embodiments of the present invention, the risk of occurrence of cardiac arrhythmias is evaluated by comparing the rate of change of the restitution properties of a heart, in response to a planned or induced abrupt change in the heart rate, relative to a threshold rate of change value. It is believed that a heart which has an increased risk of the occurrence of cardiac arrhythmias may have restitution properties which change much faster and may be associated with a greater amount of change in a given time interval in response to an abrupt change in heart rate, than a heart which has a decreased risk of the occurrence of cardiac arrhythmias.

Figure 5:
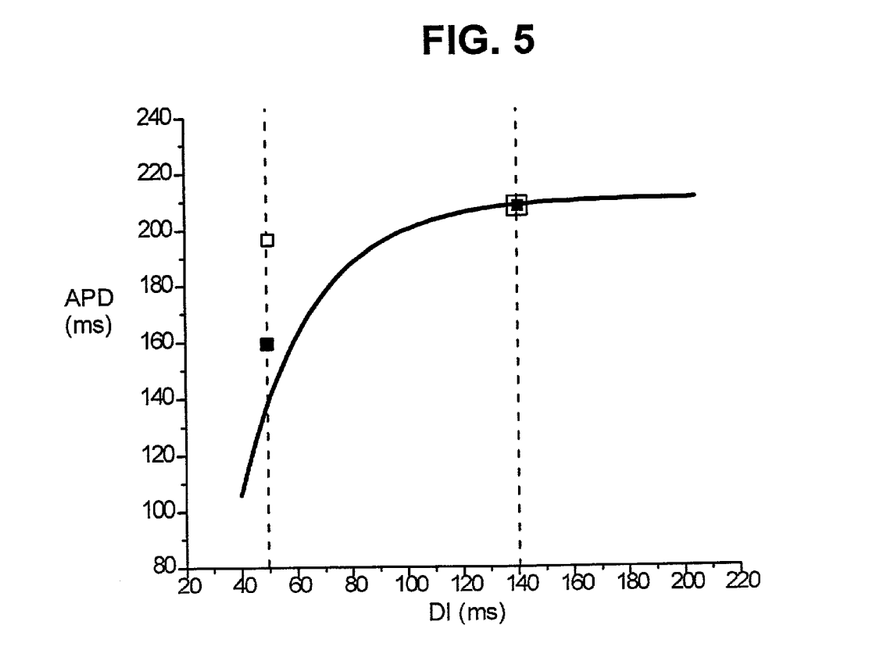
FIG. 5 is a graph showing the response of action potential duration of two hearts to an abrupt change in diastolic interval.

FIG. 5 shows a relationship between APD and DI, similar to FIG. 4, and the expected response of two different hearts to an abrupt change in heart rate. For a first heart which has a decreased risk of the occurrence of cardiac arrhythmias, when the DI is abruptly changed from 140 to 50 the APD correspondingly changes from about 205 to about 195 (shown as an open symbol). In contrast, for a second heart which has an increased risk of the occurrence of cardiac arrhythmias, when the DI is abruptly changed from 140 to 50 the APD correspondingly changes from about 205 to about 160 (shown as a filled symbol). Consequently, the second heart which has an increased or high risk of the occurrence of cardiac arrhythmias exhibits a much faster APD change response to an abrupt change in DI, and may be associated with a greater amount of change in a given time interval, than the first heart which has a decreased or low risk of the occurrence of cardiac arrhythmias.

According to some embodiments, the controller 70 evaluates the risk of occurrence of cardiac arrhythmias from action potential signals which can be relayed by sensing electrodes (such as elements 10 and 20, FIG. 1). In operation, the controller 70 records the APD and DI values of a heart before and after the heart undergoes a planned, induced, or spontaneous abrupt change in DI. The abrupt change in DI can performed, for example, by having a patient engage in high physical exertion for a sufficient time for the heart to sustain a high heart rate followed by the patient resting or may be electrically or chemically induced. The rate of change of the APD values as a function of the DI values, before and after the abrupt DI change, is compared to a predetermined threshold value. The predetermined threshold value can be an indication of how small of a rate of change of APD values as a function of DI values is a sufficient indication that a heart is expected to have a sufficient risk of occurrence of cardiac arrhythmias for the controller 70 to display a corresponding increased risk indication on the display 80. In some embodiments, the threshold value can be provided by, for example, an average, mean or weighted value of experimental results of rates of changes of APD and DI values of patients having demonstrated an increased risk of occurrence of cardiac arrhythmias to a control group of patients who have not demonstrated such increased risk of such occurrence.

According to other embodiments of the present invention, the risk of occurrence of cardiac arrhythmias is evaluated from the rate of change of the QT time interval values as a function of the TQ time interval values of a cardiac cycle. QT and TQ time interval values can be sensed by electrodes from the surface of a patient's body such as is done with a conventional electrocardiogram device. The operations for evaluating the risk in this manner can include those shown in FIG. 8 beginning at Block 800, which can be similar to those described with regard to FIG. 2.

Figure 6:
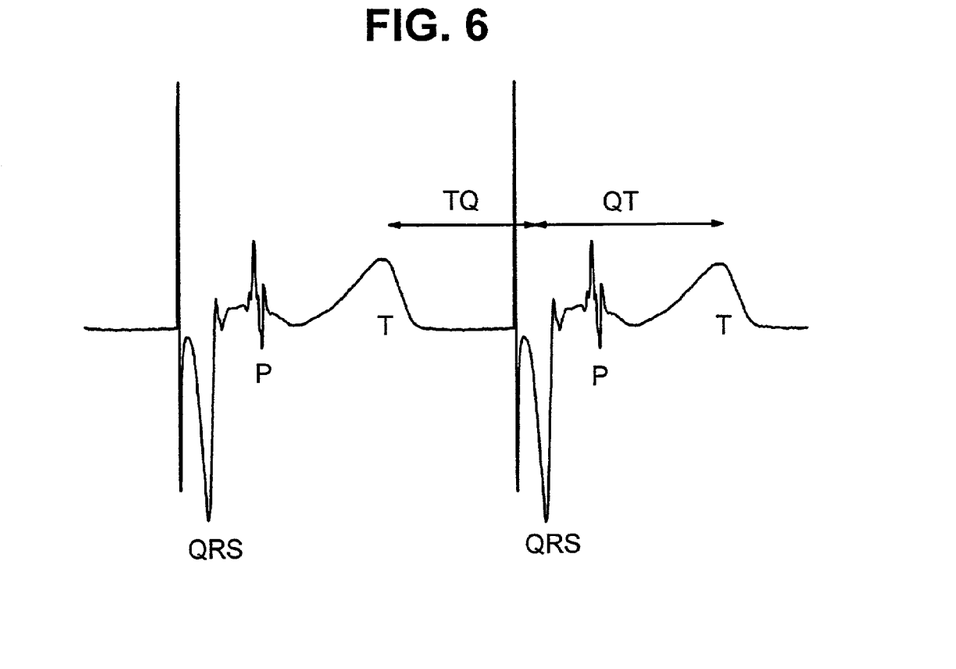
FIG. 6 is a graph showing electrocardiogram signals of a heart.
Figure 8:
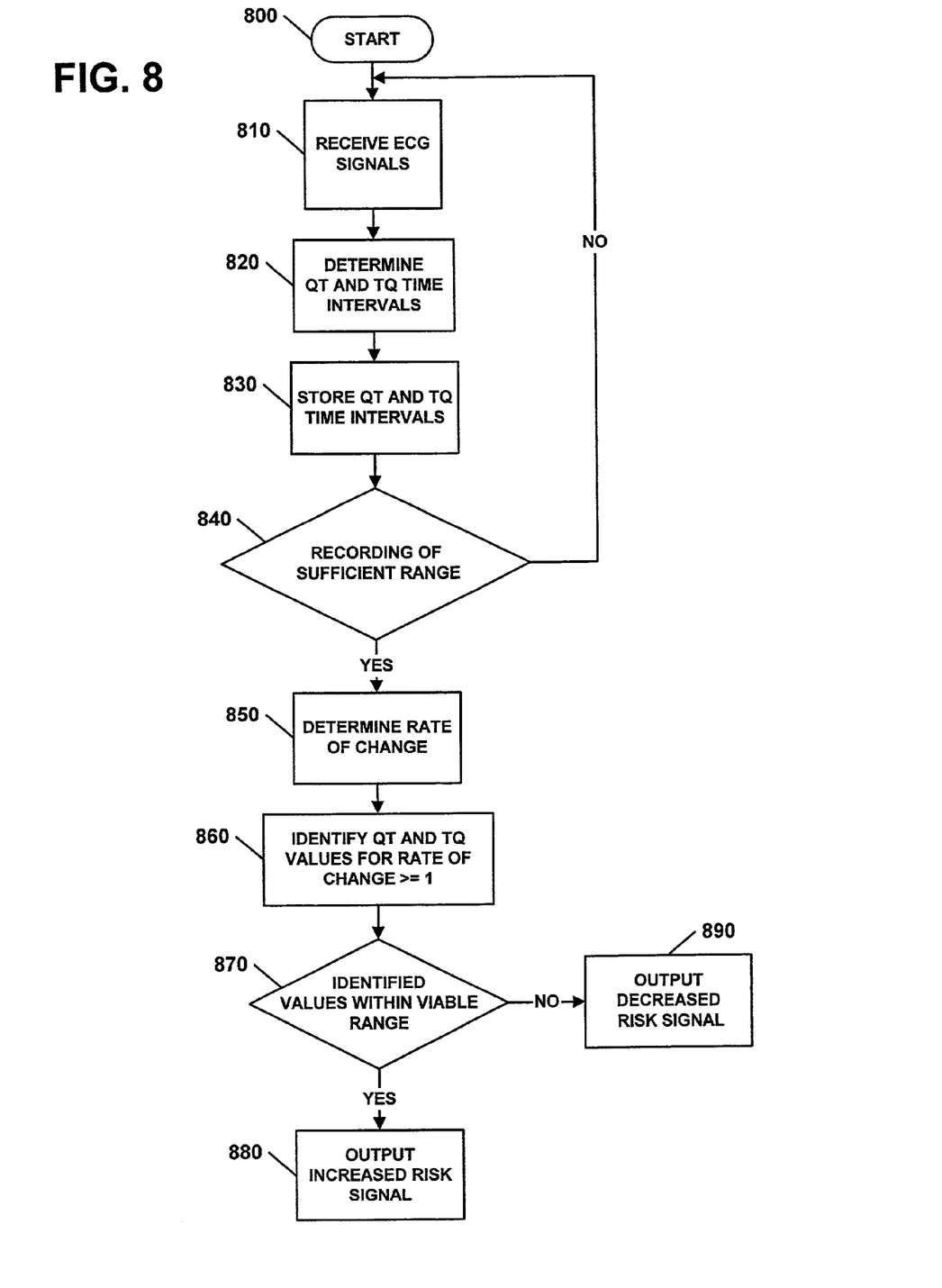
FIG. 8 is a flow chart showing operations for predicting the risk of occurrence of cardiac arrhythmias according to some embodiments of the present invention.

With reference to FIG. 8, at Block 810 electrical signals from an ECG are received which are indicative of the QT and TQ time interval values. FIG. 6 provides an example graph of electrical signals which may be sensed and illustrates the QT and TQ time intervals of a heart. The P waves may be caused by the depolarization of the muscle tissue of the atria of the heart. The QRS waves may be caused by the depolarization of the ventricles of the heart. The T waves may be caused by repolarization of the ventricles of the heart. The QT time interval extends between the QRS wave and the T wave. The TQ time interval extends from the peak of the T wave to the peak of the QRS wave. At Block 820 the QT and TQ time intervals are determined and then stored at Block 830. Storing may occur only transitionally or more permanently such as in a volatile or non-volatile memory or storage device.

As was described with regard to FIG. 2, while recordings are being made, the heart can be operated or paced over a range of desired heart rates. At Block 840, a decision is made to continue or terminate recordings. The basis for the decision can include completion of recordings over a range of heart rates, a range of sensed action potentials, completion of a time interval, or an indication from an operator to terminate the recordings.

Figure 7:
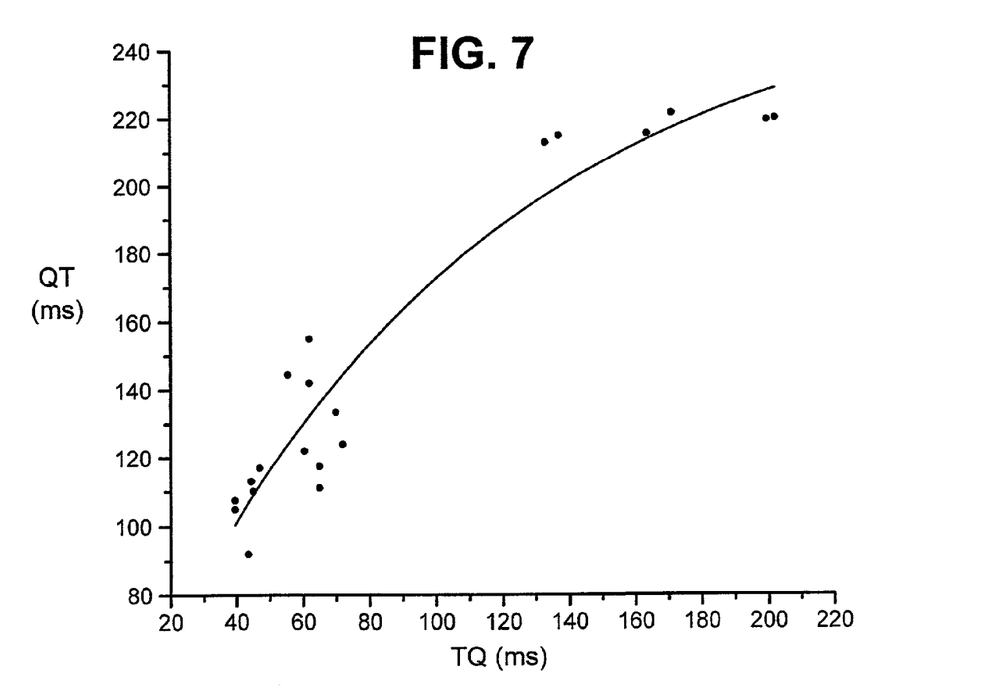
FIG. 7 is a graph showing the relationship of QT time interval to TQ time interval from experimental electrocardiogram signal data.

FIG. 7 shows a graph of an example relationship of QT and TQ time intervals from experimental data which was recorded simultaneously from the same rabbit heart with the experimental action potential data which is shown in FIG. 4. The heart rate of the rabbit was paced by direct electrical stimulation over cycle lengths from 154 to 420 milliseconds. The individual sampled QT time interval data points and TQ time interval data points along with a curve, such as an exponential curve, conventionally fitted through the data points are shown in FIG. 7.

The experimental data collected by the simultaneous recordings shown in FIGS. 7 and 4 show that the rate dependence of the QT time interval (FIG. 7) correlates with the APD intervals (FIG. 4). For example, at a heart cycle length of 420 milliseconds the APD of 216 milliseconds (FIG. 4) is about equal to the QT of 220 milliseconds (FIG. 7) and at a heart cycle length of 161 milliseconds the APD of 113 to 120 is about equal to the QT of 113 to 117 milliseconds (the range for APD and QT may be the result of alternans). Consequently, the rate of change of QT as a function of TQ can be used to evaluate the risk of cardiac arrhythmias as was previously described with regard to action potential duration.

At Block 850 of FIG. 8, the rate of change of the QT time interval values as a function of the TQ time interval values is determined. The rate of change can be determined directly from the sampled QT and TQ values by dividing the change in QT values by the change in the corresponding TQ values. Alternatively, or additionally, the rate of change can also be determined from the slope of a curve which is conventionally fitted through the QT and TQ values, such as illustrated in FIG. 7.

At Block 860 the QT and TQ values at which the rate of change is one or becomes greater than one are identified (hereafter "threshold QT and TQ values"). When the rate of change of QT as a function of TQ becomes greater than one, then cardiac arrhythmias can occur and be sustained in the heart.

At Block 870 the threshold QT and TQ values are compared to a range of heart rates over which the heart may operate (a viable range). When the threshold QT and TQ values occur within an expected viable range of the heart then the patient is evaluated to have an increased risk for the occurrence of cardiac arrhythmias and, at Block 880, a signal indicating the increased or high risk is output to the display 80 (FIG. 1). In contrast, when the threshold QT and TQ values occur outside an expected viable range of the heart or when threshold QT and TQ values could not be obtained during a patient's evaluation (i.e. the rate of change remains less than one) then a signal indicating an expected decreased or low risk of cardiac arrhythmias is output, at Block 890, to the display 80. Alternatively, or additionally, the output of the increased or decreased risk may be provided to an electronic or paper patient report.

Figure 9:
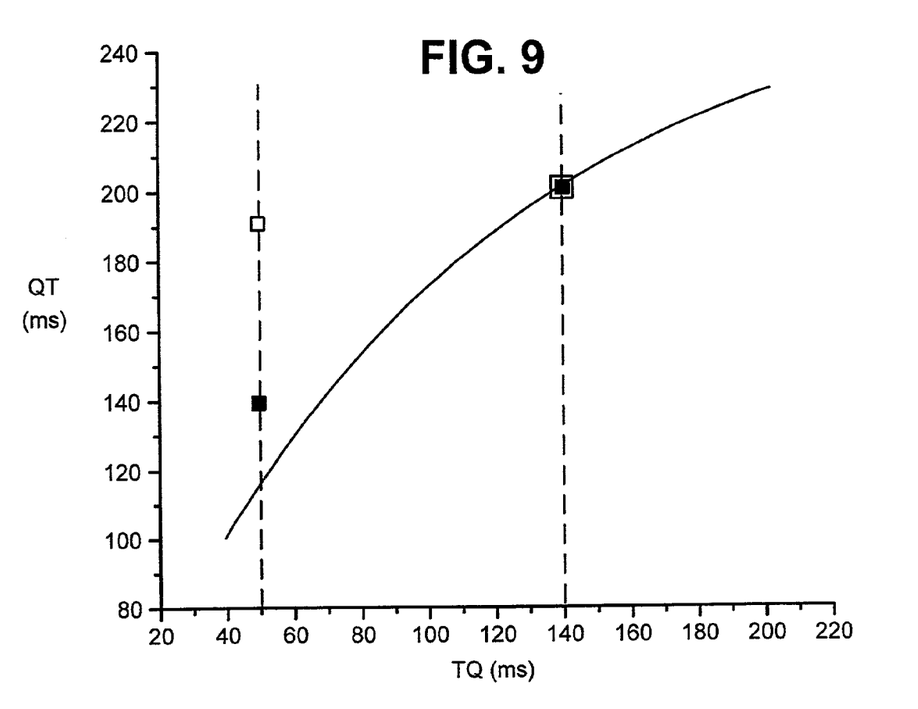
FIG. 9 is a graph showing the response of QT time interval of two hearts to an abrupt change in heart rate.

According to other embodiments of the present invention, the risk of occurrence of cardiac arrhythmias is evaluated by comparing the rate of change of the QT and TQ time intervals of a heart, in response to an abrupt change in the heart rate, relative to a threshold rate of change value. FIG. 9 shows a relationship between QT and TQ time intervals, similar to FIG. 7, and the expected response of two different hearts to an abrupt change in heart rate. For a first heart which has a decreased risk of the occurrence of cardiac arrhythmias, when the TQ time interval is abruptly changed from 140 to 50 the QT time interval correspondingly changes from about 200 to about 190. In contrast, for a second heart which has an increased risk of the occurrence of cardiac arrhythmias, when the TQ time interval is abruptly changed from 140 to 50 the QT time intervals correspondingly changes from about 200 to only about 140. Consequently, the second heart which has an increased risk of the occurrence of cardiac arrhythmias has a much faster QT time interval change response to an abrupt change in TQ time interval, and may be associated with a greater amount of change in a given time interval, than the change response of the first heart which has a decreased risk of the occurrence of cardiac arrhythmias.

According to some embodiments, the controller 70 evaluates the risk of occurrence of cardiac arrhythmias from action potential signals received from the sensing electrodes 10 and 20 (FIG. 1). In operation the controller 70 records the QT and TQ time interval values of a heart before and after the heart undergoes a planned/induced/spontaneous abrupt change in TQ value. Recordings may be taken after an elapsed time or after the heart reaches a steady state at a heart rate. The rate of change of the QT values as a function of the TQ values, before and after the abrupt TQ change, is compared to a predetermined threshold value. The predetermined threshold value can be an indication of how large of rate of change of QT values as a function of TQ values is a sufficient indication that a heart is expected to have a sufficient risk of occurrence of cardiac arrhythmias for the controller to display a corresponding increased risk indication on the display 80. In some embodiments, the threshold value can be provided by, for example, an average, mean or weighted valued of experimental results of rates of changes of QT and TQ values of patients having demonstrated an increased risk of occurrence of cardiac arrhythmias to a control group of patients who have not demonstrated such increased risk of such occurrence.

According to some other embodiments, the controller 70 evaluates the risk of occurrence of cardiac arrhythmias from the duration of the T wave (as shown in FIG. 6) received from the sensing electrodes 10 and 20 (FIG. 1). The controller 70 records the duration of the T wave over a predetermined range of heart rates or before and after an abrupt change in heart rate. Patients with an increased risk of cardiac arrhythmias may exhibit a longer T wave duration than patients with a decreased risk. The recorded T wave durations are compared to a threshold duration value. The threshold duration value can be an indication of how large of a T wave duration, as a function of heart rate or abrupt change in heart rate, is a indication that a heart is expected to have an sufficiently increased risk of the occurrence of cardiac arrhythmias. When the T wave duration is greater than the threshold duration value, the controller 70 displays an increased risk of arrhythmias indication on the display 80.

The foregoing is illustrative of the present invention and is not to be construed as limiting thereof. For example, combinations of two or more restitution properties, such as two or more of the APD, DI, QT, TQ, and T wave duration values, may be used to evaluate risk of cardiac arrhythmias. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed That which is claimed is:

1. A method for evaluating a risk of occurrence of cardiac arrhythmias in a heart, the method comprising:
   detecting electrical activity from a heart over a range of heart rates;
   determining values of at least one restitution property of the heart from the detected electrical activity over the range of heart rates; and
   evaluating the risk of occurrence of cardiac arrhythmias in the heart based on the determined values of the at least one restitution property by determining a rate of change of the determined restitution property values as a function of the heart rate; wherein the evaluating step comprises:
   determining an increased risk of the occurrence of cardiac arrhythmias when, in response to an abrupt change in the heart rate, the rate of change of the determined restitution property values is greater than a threshold value.

2. A method according to claim 1, wherein the detecting is carried out by detecting electrocardiogram signals over the range of heart rates.

3. A method according to claim 2, wherein the determining step comprises determining QT time interval values and TQ time interval values.

4. A method according to claim 3, wherein the evaluating step comprises:
   determining a rate of change of at least one of the QT time interval values and the TQ time interval values; and
   determining an increased risk of the occurrence of cardiac arrhythmias when the rate of change, in response to an abrupt change in the heart rate, is greater than a threshold value.

5. A method according to claim 1, wherein the detecting is carried out by detecting action potential signals and diastolic interval signals over the range of heart rates.

6. A method according to claim 5, wherein the evaluating step comprises:
   determining a rate of change of the action potential duration values; and
   determining an increased risk of the occurrence of cardiac arrhythmias when the rate of change, in response to an abrupt change in the heart rate, is greater than a threshold value.

7. A method according to claim 1, wherein:
   the detecting step is carried out by detecting T wave duration over the range of heart rates; and
   the evaluating step is carried out by determining an increased risk of the occurrence of cardiac arrhythmias when the T wave duration, in response to a change in the heart rate, is greater than a threshold value.

8. A method for evaluating a risk of occurrence of cardiac arrhythmias in a heart, the method comprising:
   detecting electrical activity from a heart over a range of heart rates;
   determining values of at least one restitution property of the heart from the detected electrical activity over the range of heart rates; and
   evaluating the risk of occurrence of cardiac arrhythmias in the heart based on the determined values of the at least one restitution property by determining a rate of change of the determined restitution property values as a function of the heart rate, wherein the evaluating step comprises:
   identifying a restitution property of the heart at which the rate of change of the determined restitution property values is greater than a threshold value; and
   determining an increased risk of the occurrence of cardiac arrhythmias when the identified restitution property occurs within a range at which the heart can operate during normal life activities.

9. A method according to claim 8, wherein the detecting is carried out by detecting electrocardiogram signals over the range of heart rates and wherein the determining step comprises determining QT time interval values and TQ time interval values, wherein the evaluating step comprises:
   determining a rate of change of the QT time interval values as a function of the TQ time interval values;
   identifying a QT time interval value and a TQ time interval value at which the rate of change of the QT time interval values and the TQ time interval values is greater than one; and
   determining an increased risk of the occurrence of cardiac arrhythmias when at least one of the identified QT time interval value and the TQ time interval value occurs within a range at which the heart can operate during normal life activities.

10. A method according to claim 8, wherein the detecting is carried out by detecting action potential signals and diastolic interval signals over the range of heart rates and wherein the evaluating step comprises:
    determining a rate of change of the action potential duration values as a function of the diastolic interval values;
    identifying a action potential duration value and a diastolic interval value at which the rate of change is greater than one; and
    determining an increased risk of the occurrence of cardiac arrhythmias when at least one of the identified action potential duration value and the diastolic interval value interval value occurs within a range at which the heart can operate during normal life activities.

11. A system for evaluating a risk of occurrence of cardiac arrhythmias in a heart, the system comprising:
    at least one sensing electrode configured to sense electrical signals from a heart over a range of heart rates; and
    a controller connected to receive signals from the at least one sensing electrode and configured to determine values of at least one restitution property of the heart, from the electrical signals, over the range of heart rates and to evaluate the risk of occurrence of cardiac arrhythmias in the heart from the determined values of the at least one restitution property wherein the controller is configured to evaluate the risk of the occurrence of cardiac arrhythmias by determining a rate of change of the determined values of the at least one restitution property as a function of the heart rate and to generate a signal indicative of an evaluated increased risk of the occurrence of cardiac arrhythmias when the rate of change, in response to an abrupt change in the heart rate, is greater than a threshold value.

12. A method according to claim 11, wherein:
    the at least one sensing electrode is configured to sense electrocardiogram signals from a heart over the range of heart rates; and
    the controller is configured to determine restitution properties of the heart from the electrocardiogram signals.

13. A system according to claim 12 wherein:
the controller is configured to determine QT time interval values and TQ time interval values.

14. A system according to claim 13, wherein:
the controller is configured to determine a rate of change of at least one of the QT time interval values and the TQ time interval values and to generate a signal indicative of an increased risk of the occurrence of cardiac arrhythmias when the rate of change of the at least one of the QT time interval values and the TQ time interval values, in response to an abrupt change in the heart rate, is greater than a threshold value.

15. A system according to claim 11, wherein:
the at least one sensing electrode is connectable to muscle fiber of the heart to sense action potential signals and diastolic interval signals of the heart; and
the controller is configured to determine a restitution property of the heart from the action potential signals and the diastolic interval signals over a range of heart rates.

16. A system according to claim 15, wherein:
the controller is configured to determine a rate of change of the action potential duration values and to generate a signal indicative of an increased risk of the occurrence of cardiac arrhythmias when the rate of change of the action potential duration values, in response to an abrupt change in the heart rate, is greater than a threshold value.

17. A system according to claim 11, wherein:
the controller is configured to determine T wave duration over the range of heart rates and to generate a signal indicative of an evaluated increased risk of the occurrence of cardiac arrhythmias when the T wave duration, in response to a change in the heart rate, is greater than a threshold value.

18. A system for evaluating a risk of occurrence of cardiac arrhythmias in a heart, the system comprising:
at least one sensing electrode configured to sense electrical signals from a heart over a range of heart rates; and
a controller connected to receive signals from the at least one sensing electrode and configured to determine values of at least one restitution property of the heart, from the electrical signals, over the range of heart rates and to evaluate the risk of occurrence of cardiac arrhythmias in the heart from the determined values of the at least one restitution property wherein the controller is configured to evaluate the risk of the occurrence of cardiac arrhythmias by determining a rate of change of the determined values of the at least one restitution property as a function of the heart rate and to identify a restitution property of the heart at which the rate of change of the range of the determined values of the at least one restitution property is greater than a threshold value and to generate a signal indicative of an increased risk of the occurrence of cardiac arrhythmias when the identified restitution property is within a range of restitution properties for which the heart can operate during normal life activities.

19. A system according to claim 18 wherein:
the at least one sensing electrode is configured to sense electrocardiogram signals from a heart over the range of heart rates; and
the controller is configured to determine restitution properties of the heart from the electrocardiogram signals;
the controller is configured to determine QT time interval values and TQ time interval values and to determine a rate of change of the QT time interval values as a function of the TQ time interval values, to identify a QT time interval value and a TQ time interval value at which the rate of change of the QT time interval values and the TQ time interval values is greater than one, and to generate a signal indicative of an evaluated increased risk of the occurrence of cardiac arrhythmias when at least one of the identified QT time interval value and the TQ time interval value is within a range for which the heart can operate during normal life activities.

20. A system according to claim 18, wherein:
the at least one sensing electrode is connectable to muscle fiber of the heart to sense action potential signals and diastolic interval signals of the heart;
the controller is configured to determine a restitution property of the heart from the action potential signals and the diastolic interval signals over a range of heart rates and to determine a rate of change of the action potential duration values as a function of the diastolic interval values, to identify a action potential duration value and a diastolic interval value at which the rate of change is greater than one, and to generate a signal indicative of an increased risk of the occurrence of cardiac arrhythmias when at least one of the identified action potential duration value and the diastolic interval value interval value is within a range for which the heart can operate during normal life activities.

21. A computer program product for evaluating a risk of occurrence of cardiac arrhythmias in a heart, the computer program product comprising:
a computer readable storage medium having computer readable code embodied in the medium, the computer-readable program code comprising:
computer readable program code for receiving electrical signals from a heart over a range of heart rates;
computer readable program code for determining values of at least one restitution property of the heart from the electrical signals over the range of heart rates;
computer readable program code for evaluating the risk of occurrence of cardiac arrhythmias in the heart based on from determined values of the at least one restitution property;
computer readable program code for evaluating the risk of the occurrence of cardiac arrhythmias by determining a rate of change of the determined restitution property values as a function of the heart rate; and
computer readable program code for generating a signal indicative of an increased risk of the occurrence of cardiac arrhythmias in the heart when the rate of change, in response to an abrupt change in the heart rate, is greater than a threshold value.

22. A computer program product according to claim 21, wherein the computer program code further comprises computer readable program code for receiving electrocardiogram signals and to determine values of the at least one restitution property of the heart from the electrocardiogram signals.

23. A computer program product according to claim 22, wherein the computer program code further comprises computer readable program code for determining QT time interval values and TQ time interval values of the heart from the electrocardiogram signals.

24. A computer program product according to claim 23 wherein the computer program code further comprises computer readable program code for determining a rate of change of at least one of the QT time interval values and the TQ time interval values and for generating a signal indicative of an increased risk of the occurrence of cardiac arrhythmias when the rate of change, in response to an abrupt change in the heart rate, is greater than a threshold value.

25. A computer program product according to claim 21 wherein the computer program code further comprises computer readable program code for receiving action potential signals and diastolic interval signals of the heart and determining values of the at least one restitution property from the action potential signals and the diastolic interval signals over a range of heart rates.

26. A computer program product according to claim 25 wherein the computer program code further comprises computer readable program code for determining a rate of change of the action potential duration values and for generating a signal indicative of an increased risk of the occurrence of cardiac arrhythmias when the rate of change, in response to an abrupt change in the heart rate, is greater than a threshold value.

27. A computer program product according to claim 21 wherein the computer program code further comprises computer readable program code for determining T wave duration over the range of heart rates and generating a signal indicative of an increased risk of the occurrence of cardiac arrhythmias when the T wave duration, in response to a change in the heart rate, is greater than a threshold value.

28. A computer program product for evaluating a risk of occurrence of cardiac arrhythmias in a heart, the computer program product comprising:
   a computer readable storage medium having computer readable code embodied in the medium, the computer-readable program code comprising:
   computer readable program code for receiving electrical signals from a heart over a range of heart rates;
   computer readable program code for determining values of at least one restitution property of the heart from the electrical signals over the range of heart rates;
   computer readable program code for evaluating the risk of occurrence of cardiac arrhythmias in the heart based on from determined values of the at least one restitution property;
   computer readable program code for evaluating the risk of the occurrence of cardiac arrhythmias by determining a rate of change of the determined restitution property values as a function of the heart rate; and
   computer readable program code for identifying a restitution property of the heart at which the rate of change is greater than a predetermined threshold value and to generate a signal indicative of an increased risk of the occurrence of cardiac arrhythmias when the identified restitution property is within a predetermined rate of restitution properties for which the heart can operate during normal life activities.

29. A computer program product according to claim 28 wherein the computer program code further comprises computer readable program code for receiving electrocardiogram signals and to determine values of the at least one restitution property of the heart from the electrocardiogram signals, determining QT time interval values and TQ time interval values of the heart from the electrocardiogram signals, determining a rate of change of the QT time interval values as a function of the TQ time interval values, identifying a QT time interval value and a TQ time interval value at which the rate of change of the QT time interval values and the TQ time interval values is greater than one, and generating a signal indicative of an increased risk of the occurrence of cardiac arrhythmias when at least one of the identified QT time interval value and the TQ time interval value is within a range for which the heart can operate during normal life activities.

30. A computer program product according to claim 28 wherein the computer program code further comprises computer readable program code for receiving action potential signals and diastolic interval signals of the heart and determining values of the at least one restitution property from the action potential signals and the diastolic interval signals over a range of heart rates, determining a rate of change of the action potential duration values as a function of the diastolic interval values, identifying a action potential duration value and a diastolic interval value of the heart at which the rate of change is greater than one, and generating a signal indicative of an increased risk of the occurrence of cardiac arrhythmias when at least one of the identified action potential duration value and the diastolic interval value interval value is within a range for which the heart can operate.

* * * * *